(12) United States Patent
Yesland (10) Patent No.: US 6,586,237 B1
(45) Date of Patent: Jul. 1, 2003

(54) COMPOSITIONS AND METHODS FOR CLONING NUCLEIC ACIDS

(76) Inventor: Kyle David Yesland, 3801 Channel Pl., Newport Beach, CA (US) 92663

( * ) Notice: Subject to any disclaimer, the term of this patent is extended or adjusted under 35 U.S.C. 154(b) by 0 days.

(21) Appl. No.: 10/154,710

(22) Filed: May 24, 2002

(51) Int. Cl.[7] .......................... C12N 15/63; C12N 15/11; C12P 19/34
(52) U.S. Cl. ................... 435/320.1; 536/23.1; 435/91.2
(58) Field of Search ...................... 536/23.1; 435/320.1, 435/91.2

(56) References Cited

U.S. PATENT DOCUMENTS 5,487,993 A * 1/1996 Herrnstadt et al. ...... 435/172.3
5,827,657 A * 10/1998 Herrnstadt et al. ............ 435/6
5,856,144 A * 1/1999 Mierendorf et al. ....... 435/91.2

OTHER PUBLICATIONS

Cha et al., New vectors for direct cloning of PCR products, 1993, GENE, vol. 136, pp. 369–370.*
Gayle, III et al., Formation of MboII vectors and using asymmetric MboII linkers, 1987, GENE, vol. 54, pp. 221–228.*
Hu, DNA polymerase–catalyzed addition of nontemplated extra nucleotides to the 3' end of a DNA fragment, 1993, DNA and Cell Biology, vol. 12, pp. 763–770.*

* cited by examiner

Primary Examiner—James Ketter
Assistant Examiner—Daniel M. Sullivan
(74) Attorney, Agent, or Firm—Kyle D. Yesland (57) ABSTRACT

Compositions comprising two or more linear DNA molecules capable of self-replicating when circularized, the linear DNA molecules comprising a single overhanging nucleotide at each 3' end, wherein a pair of overhanging nucleotides of a linear DNA molecule of the composition are different than a pair of overhanging nucleotides of another linear DNA molecule of the composition.

32 Claims, 1 Drawing Sheet

Fig. 1

COMPOSITIONS AND METHODS FOR CLONING NUCLEIC ACIDS

FIELD OF THE INVENTION

The present invention relates to cloning nucleic acid molecules that have been exposed to an enzyme, or other substance, which produces an overhanging nucleotide(s) at one or more 3' or 5' ends of the molecules.

BACKGROUND

The polymerase chain reaction (PCR) has become an invaluable tool for molecular biologists. Numerous applications have been discovered for PCR. Examples include DNA fingerprinting, DNA sequencing, site directed mutagenesis and cloning applications.

PCR is based on three discrete, multiply repeated steps: denaturation of a DNA template, annealing of a primer to the denatured DNA, and extension of the primer with a polymerase to create a nucleic acid complementary to the template. Each primer extension product specifically anneals with a complementary primer and the resulting primed template DNA acts as a substrate for a further extension reaction. These steps are repeated many times, for example, by using an automated cycling procedure, thereby exponentially amplifying the initial nucleic acid material. The conditions under which these steps are performed are well established in the art. Procedures for conducting PCR have been extensively described. See, for example, U.S. Pat. Nos. 4,683,195 and 4,683,202, which are incorporated in their entirety herein by reference.

It is often desirable to obtain clones of a PCR amplified DNA product. A common method for cloning PCR products involves incorporation of flanking restriction sites onto the ends of primer molecules. In this method the PCR cycling is carried out and the amplified DNA is purified, restricted with an appropriate endonuclease(s) and ligated to a compatible vector preparation. Thus, this PCR cloning method requires the step of preparing PCR primer molecules which include base sequences having a preferred restriction recognition sequence. Also, this method can result in unintended internal restriction of uncharacterized restriction site sequences. In addition, cleavage of the PCR product by the preferred restriction enzyme may often be inefficient because the restriction site is close to the end of the DNA molecule to be cleaved. Such limitations add to the cost and complexity of cloning PCR products on a routine basis.

Many DNA polymerases, including Taq DNA polymerase and other thermostable DNA polymerases may catalyze a non-template directed addition of single deoxynucleotide monophosphate (dNMP) residue to the 3' termini of blunt-ended DNA duplexes. Thus, DNA polymerase may naturally create a single base, cohesive termini on otherwise blunt end DNA fragments. For example, during PCR, a thermostable DNA polymerase used may add a single nucleotide to the 3' end of an otherwise blunt end DNA PCR product. These overhanging residues are widely viewed as incompatible with most molecular cloning schemes. The overhanging residues may be removed with enzymes such as S1 nuclease and Klenow fragment to create blunt ends. The blunted PCR products can then be cloned into a vector which has been digested with a restriction enzyme that will leave a blunt end compatible with the blunted PCR fragment.

Many problems exist with blunt end cloning of PCR products. For example, enzymatic blunting of the PCR product may often be inefficient. Also, recircularization of the blunt ended linear vector with no target sequence inserted is common leading to a low cloning efficiency. To help overcome this last problem dephosphorylation is sometimes used.

Dephosphorylation of the vector can help prevent self-ligation thereby increasing the efficiency of target sequence insertion. However, this procedure can be problematic because of, for example, the difficulty that may be involved in inactivating the phosphorylase.

One technique that has been developed to directly clone PCR products takes advantage of the Taq polymerase catalyzed non-template directed addition of dAMP residue to the 3' termini of some blunt-ended DNA PCR products (described in U.S. Pat. Nos. 5,487,993 and 5,827,657). This technique uses a linearized vector with compatible, cohesive, single nucleotide dTMP residues overhanging each end of the linearized vector. PCR DNA products which have a dAMP nucleotide overhang at both 3' ends may be cloned into these vectors. This method is based on the publication of Clark (Nucleic Acids Res. Vol. 16 pg. 9677–9686). In Clark, the data showed that a dAMP nucleotide was preferentially added to an 18 base primer in a non-template directed fashion by a variety of DNA polymerases, including Taq DNA polymerase.

It has become apparent that nucleotides other than DAMP may be preferentially added to a 3' end of certain PCR products in a non-template dependent manner. In particular, dGMP may often be the preferred nucleotide added. dCMP and dTMP may also be preferentially added but possibly to a lesser degree than dAMP and dGMP. Variables that may effect which nucleotide is added to the 3' end of the PCR product include the primer sequences, the sequence of the target DNA and the DNA polymerase used.

The above-described cloning techniques are ineffective to directly clone PCR products that have a non-dAMP nucleotide added to one or both of the PCR product's 3' end(s).

In view of the above considerations, what is needed are compositions and methods for directly cloning PCR products which have been extended at each 3' end by any nucleotide, for example, dGMP, dAMP, dCMP or dTMP.

SUMMARY

The present invention meets this need and provides for compositions and methods that allow for the cloning of PCR products which include PCR products with any combination of the nucleotides dAMP, dTMP, dCMP or dGMP overhanging the PCR product's 3' ends.

In accordance with the present invention there are provided compositions which include one or more or two or more linear DNA molecules. These DNA molecules include a single nucleotide overhanging each 3' end. The compositions may include one or more DNA molecules selected from: a linear DNA molecule with an overhanging dTMP residue at each 3' end, a linear DNA molecule with an overhanging dGMP at each 3' end, a linear DNA molecule with an overhanging dCMP at each 3' end, a linear DNA molecule with an overhanging dAMP at each 3' end, a linear DNA molecule with an overhanging dTMP at one 3' end and an overhanging dAMP at another 3' end, a linear DNA molecule with an overhanging dTMP at one 3' end and an overhanging dGMP at another 3' end, a linear DNA molecule with an overhanging dTMP at one 3' end and an overhanging dCMP at another 3' end, a linear DNA molecule with an overhanging dAMP at one 3' end and an overhanging dGMP at another 3' end, a linear DNA molecule with an overhanging dAMP at one 3' end and an overhanging dCMP at another 3' end and/or a linear DNA molecule with an overhanging dGMP at one 3' end and an overhanging dCMP at another 3' end. This embodiment allows for the cloning of PCR products with any combination of dNMPs non-specifically attached to each 3' end of the PCR product.

In one embodiment, the one or more or two or more DNA molecules, which comprise a composition of the invention, are the same or substantially the same nucleotide sequence except for the single nucleotide overhanging each 3' end of the DNA molecule or molecules.

In one embodiment, the one or more or two or more DNA molecules which comprise a composition of the invention are a linearized DNA molecule, for example, a linearized vector. Examples of vectors include a plasmid, a phagemid, a bacteriophage, a prokaryotic expression vector, a eukaryotic vector, a eukaryotic expression vector or a virus. In certain embodiments, the vectors may include a prokaryotic replicon, a transcription start site and/or antibiotic resistance.

Compositions of the invention may include a nucleic acid PCR product. The compositions of the invention may include being transformed into a host cell. The host cell may be eukaryotic or prokaryotic.

In one embodiment, a composition of the invention includes a ratio of DNA molecules that maximizes the percentage of positive clones in a ligation reaction between a PCR product and a composition of the invention which includes two or more linear DNA molecules.

Further in accordance with the present invention, there is provided a composition which includes a linear DNA molecule which has an overhanging dTMP at one 3' end and an overhanging dCMP at another 3' end. This embodiment may include a linear DNA molecule with an overhanging dCMP at each 3' end and/or a linear DNA molecule with an overhanging dTMP at each 3' end. This embodiment allows for the cloning of PCR products non-specifically extended at each end with any combination of DAMP and dGMP which may be the most common nucleotides added non-specifically to the 3' end of PCR products.

Also included within the scope of the present invention are methods for using the compositions of the present invention to clone a DNA molecule which is produced by a polymerase chain reaction (PCR). These methods may include subjecting a DNA molecule to a polymerase chain reaction amplification to produce DNA molecules. The DNA molecules may include a DNA molecule with an overhanging dTMP residue at each 3' end, a DNA molecule with an overhanging dGMP at each 3' end, a DNA molecule with an overhanging dCMP at each 3' end, a DNA molecule with an overhanging dAMP at each 3' end, a DNA molecule with an overhanging dTMP at one 3' end and an overhanging dAMP at another 3' end, a DNA molecule with an overhanging dTMP at one 3' end and an overhanging dGMP at another 3' end, a DNA molecule with an overhanging dTMP at one 3' end and an overhanging dCMP at other 3' end, a DNA molecule with an overhanging dAMP at one 3' end and an overhanging dGMP at another 3' end, a DNA molecule with an overhanging dAMP at one 3' end and an overhanging dCMP at another 3' end and/or a DNA molecule with an overhanging dGMP at one 3' end and an overhanging dCMP at another 3' end or mixtures thereof or combinations thereof.

The method further includes the step of ligating the DNA molecules to a composition of the present invention. In one embodiment, the method further includes the step of transforming these ligated DNA molecules into a host cell.

Still further in accordance with the present invention there is provided a kit for direct cloning of polymerase chain reaction amplified nucleic acids. The kit includes a container which includes one or more or two or more linear DNA molecules which are capable of self replication in a host cell when circularized, each of the linear DNA molecules being selected from the group consisting of a linear DNA molecule with an overhanging dTMP residue at each 3' end, a linear DNA molecule with an overhanging dGMP at each 3' end, a linear DNA molecule with an overhanging dCMP at each 3' end, a linear DNA molecule with an overhanging dAMP at each 3' end, a linear DNA molecule with an overhanging dTMP at one 3' end and an overhanging dAMP at another 3' end, a linear DNA molecule with an overhanging dTMP at one 3' end and an overhanging dGMP at another 3' end, a linear DNA molecule with an overhanging dTMP at one 3' end and an overhanging dCMP at another 3' end, a linear DNA molecule with an overhanging DAMP at one 3' end and an overhanging dGMP at another 3' end, a linear DNA molecule with an overhanging DAMP at one 3' end and an overhanging dCMP at another 3' end and/or a linear DNA molecule with an overhanging dGMP at one 3' end and an overhanging dCMP at another 3' end.

Any combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

Definitions

Base Pair (bp) is a hydrogen bonded nucleotide pair. For example, a base pair may be dAMP (A) paired with dTMP (T), or of dCMP (C) paired with dGMP (G) in a double stranded DNA molecule. In RNA, uracil (U) may be substituted for dTMP. Single stands of DNA or RNA are said to be "complementary" when the base pairs of each DNA strand may form base pairs with the other DNA or RNA strand when the two DNA or RNA strands adopt a double stranded configuration with each other.

"Cleave" means to enzymatically digest, for example, with a restriction endonuclease, a DNA, for example, a vector.

"Clone" means to insert a DNA sequence, for example, a target DNA sequence into a recipient vector of the invention.

"Complementary" means one or more nucleotides in a single strand of RNA or DNA having the ability to form a hydrogen bonded nucleotide pair with one or more nucleotides in another single strand of RNA or DNA.

A conserved nucleotide sequence is a nucleotide sequence that is conserved with respect to a pre-selected sequence if it non-randomly hybridizes to an exact complement of the pre-selected sequence.

"Combinations" means mixtures or a sequential use of compositions. An example of a sequential use is the use of one composition followed by use of another composition. Each composition may be a specified composition.

A dNMP is a deoxynucleotide monophosphate. A dNDP is a deoxynucleotide diphosphate. A dNTP is a deoxynucleotide triphosphate. Any and all dNMPs discussed within the scope of the present invention are also contemplated as a being either a dNMP, a dNDP or a dNTP in the same or similar circumstance. Examples of dNMPs are dAMP (deoxy-adenosine monophospate) which may be referred to as A, dTMP (deoxy-thymidime monophospate) which may be referred to as T, dGMP (deoxy-guanosine monophospate) which may be referred to as G and dCMP (deoxy-cytodine monophospate) which may be referred to as C.

A duplex DNA is a double-stranded nucleic acid molecule comprising two strands of substantially complementary polynucleotides held together by one or more hydrogen bonds between each of the complementary bases present in a base pair of the duplex. Because the nucleotides that form a base pair can be either a ribonucleotide base or a deoxyribonucleotide base, the phrase "duplex DNA" refers to either a DNA-DNA duplex comprising two single strands of DNA (ds DNA), or an RNA-DNA duplex comprising one DNA strand and one RNA strand, or an RNA-RNA duplex comprising two single strands of RNA (ds RNA).

A gene coding sequence is a nucleic acid whose nucleotide sequence codes for an RNA or a protein molecule. Genes may comprise uninterrupted sequences of nucleotides or they may include such intervening segments as introns, promoter regions, splicing sites and repetitive sequences. A gene can be either RNA or DNA.

Hybridization is the pairing of complementary nucleotide sequences (strands of nucleic acid) to form a duplex, heteroduplex, or complex containing more than two single-stranded nucleic acids, by establishing hydrogen bonds between/among complementary base pairs. Hybridization is a specific, i.e. non-random, interaction between/among complementary polynucleotides that can be competitively inhibited.

A nucleotide is a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus. Nucleotides include nucleotide analogs.

A nucleotide analog is a purine or pyrimidine nucleotide that differs structurally from an A, T, G, C, or U base, but is sufficiently similar to substitute for the normal nucleotide in a nucleic acid molecule. Inosine (I) is a nucleotide analog that can hydrogen bond with any of the other nucleotides, A, T, G, C, or U. In addition, methylated bases are known that can participate in nucleic acid hybridization. Analogs of nucleotides are within the scope of the present invention for use in vectors comprising compositions of the present invention or in target sequences for use in accordance with the present invention.

A phagemid is a circular DNA molecule that includes one or more portions of a bacteriophage and one or more portions of a plasmid.

A polynucleotide is a polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides (relatively short polynucleotides), genes, vectors, plasmids, and the like.

Positive clones are cloned vectors which have a desired PCR product ligated to each end of the vector.

A primer is a polynucleotide, whether purified from a nucleic acid restriction digest or produced synthetically, that is capable of acting as a point of initiation of synthesis when placed under conditions in which synthesis of a primer extension product complementary to a template nucleic acid strand is induced, i.e., in the presence of nucleotides and an agent for polymerization, such as DNA polymerase, reverse transcriptase and the like, under suitable temperature and pH reaction conditions.

Recombinant DNA is a DNA molecule produced by covalently linking a nucleic acid sequence, such as a gene, to a vector, for example, a DNA molecule sequence of the present invention. Thus, a recombinant DNA molecule is a hybrid DNA molecule comprising at least two nucleotide sequences not normally found together in nature rDNA's not having the same biological origin as the host are said to be "heterologous".

"Substantially" means mostly. For example, substantially may mean more than 50%, more than 60% more than 70%, more than 80%, more than 90%, more than 99%, or more than 99.9%.

"Target DNA sequence" means a duplex segment of DNA which includes one or more overhanging nucleotides. For example, a target DNA sequence may be a PCR DNA product with a single overhanging nucleotide attached to each 3' end.

"Template" or "template sequence" is a nucleic acid sequence that primers hybridize to and may also include the nucleic acid sequence amplified in a PCR reaction.

"uM" means micromolar, "ul" means microliter, and "ug" means microgram.

A vector is a double stranded DNA molecule capable of autonomous replication in a cell. A heterologous DNA segment can be cloned or covalently linked to the vector so as to bring about replication of the cloned or attached DNA segment. Vectors include plasmids, phagemids, bacteriophage and viruses. Vectors capable of directing the expression of genes encoding for one or more proteins are referred to herein as "expression vectors". Vectors may allow cloning of cDNA (complementary DNA) from mRNAs produced using reverse transcriptase. Vectors may include one or more replicons, one or more antibiotic resistant genes (for example, ampicillin resistance), one or more promoter sequences, the gene encoding a portion of a beta-galactosidase, for example, the LacZ portion, reporter genes, genes encoding florescent substances, genes encoding phosphorescent compounds and/or an f1 origin of replication.

DETAILED DESCRIPTION

The present invention is, in part, based upon the discovery that compositions comprising certain linearized vectors, each vector with a single nucleotide overhang at each end, are highly efficient cloning vehicles for certain DNA molecules, for example, DNA molecules produced by the polymerase chain reaction.

Each 3' end of a DNA molecule produced by PCR may be extended with any of the four nucleotides (dAMP, dTMP, dCMP or dGMP). Therefore, the possibility for at least 10 combinations of nucleotide pairs (one at each 3' end of a PCR product DNA molecule, e.g., T and T, A and A, C and C, G and G, A and C, A and G, A and T, G and C, G and T & C and T) exists. The present invention provides for compositions, methods and kits useful to clone each of these PCR product DNA molecules.

Compositions of the present invention include linear vectors which include a single nucleotide overhanging at each 3' end of the vectors. In one embodiment, a composition of the present invention includes an essentially homogeneous mixture of linear vector molecules, these vectors having the same nucleotide overhanging each 3' end. This embodiment includes vectors with a single overhanging 3'-dTMP at each end of the vector; a single overhanging 3'-dAMP at each end of the vector; a single overhanging 3'-dGMP at each end of the vector and a single overhanging 3'-dCMP at each end of the vector.

In another embodiment, the present invention includes an essentially homogeneous mixture of linear vector molecules, these vectors having a first single nucleotide overhanging one 3' end of each vector and a second single nucleotide overhanging the other 3' end of each vector, the first and second nucleotides being different nucleotides. This embodiment includes vectors with an overhanging dTMP at one 3' end and an overhanging dAMP at the other 3' end, vectors with an overhanging dTMP at one 3' end and an overhanging dGMP at the other 3' end, vectors with an overhanging dTMP at one 3' end and an overhanging dCMP at the other 3' end, vectors with an overhanging dAMP at one 3' end and an overhanging dGMP at the other 3' end, vectors with an overhanging dAMP at one 3' end and an overhanging dCMP at the other 3' end and vectors with an overhanging dGMP at one 3' end and an overhanging dCMP at the other 3' end.

Another embodiment of the present invention includes combinations of vectors from the above described first embodiment and/or the above described second embodiment. For example, a combination of a vector with an overhanging dCMP at each 3' end, and a vector with an overhanging dTMP at one 3' end and an overhanging dCMP at the other 3' end, and a vector with an overhanging dTMP at each 3' end. In another example, a vector with an overhanging dAMP at one 3' end and an overhanging dCMP at the other 3' end and a vector with an overhanging dGMP at one 3' end and an overhanging dCMP at the other 3' end and a vector with an overhanging dTMP at each 3' end are used in combination. In another example, a vector with an overhanging dTMP at each 3' end and a vector with an overhanging dAMP at each 3' end. and a vector with an overhanging dGMP at each 3' and a vector with an overhanging dTMP at one 3' end and an overhanging dAMP at the other 3' end and a vector with an overhanging dTMP at one 3' end and an overhanging dGMP at the other 3' end, a vector with an overhanging dTMP at one 3' end and an overhanging dCMP at the other 3' end, and a vector with an overhanging dAMP at one 3' end and an overhanging dGMP at the other 3' end are combined. These are examples of combinations of vectors within the scope of the invention. The present invention includes any and all possible combinations of the vectors described in the first embodiment and second embodiment described above.

One important element of the present invention is that compositions may comprise a linear vector with different nucleotide types at each 3' end.

Another important element is that a composition may comprise mixtures of different types of linear vectors, each linear vector type in the mixture having a different pair of 3' overhanging nucleotides than other types of linear vectors in the mixture. By mixing these vectors together to form a single composition to be used in a ligation reaction with a target sequence, for example, a PCR product, the present invention allows for the direct cloning of a target DNA sequence with unidentified nucleotides overhanging the 3' ends of the target sequence.

This invention also contemplates the use of herein described vectors, mixtures of vectors and combinations of vectors which are chosen based on the nucleotide(s) predicted to be attached to the target DNA sequence. This prediction may be based on, for example, the nucleotide sequence of the primer and/or the nucleotide sequence of the target sequence and or the DNA polymerase used.

This invention also envisions the use of preferred ratios of vectors used in combination with each other to optimize the cloning efficiency of the compositions of the invention. These preferred ratios can be determined empirically on a trial and error basis in the laboratory by a technician of ordinary skill in the field.

Target DNA sequences of the present invention typically are DNA molecules having cohesive termini, i.e., "overhanging" single-stranded portions that extend beyond the double-stranded portion of the molecule. In one embodiment, a target DNA sequence of the present invention comprises a linear duplex DNA molecule that has been extended by a nucleotide at one or more 3' ends of duplex DNA molecule by contacting the DNA to one or more DNA polymerases, including heat stable DNA polymerases such as, Taq, KlenTaq, Vent, DeepVent, Pfu, and Replinase. For example, a target DNA sequence may be a PCR product. The target DNA sequence may include a structural gene, an intervening sequence, a promoter, a regulatory sequence, a repetitive sequence, a flanking sequence, a coding sequence, a synthetic nucleic acid or a combination of these or none of these. The only requirement is that the target sequence includes a duplex DNA.

The present invention contemplates using the PCR technique described herein below, to generate a target DNA sequence. The PCR technique employs primer molecules to initiate the primer elongation reaction. The primer must be sufficiently long to prime the synthesis of extension products in the presence of the agents for polymerization. The exact lengths of the primers will depend on many factors, including temperature and the source of primer. For example, depending on the complexity of the template sequence, a primer may contain 8 to 40 nucleotides, although it can contain more or fewer nucleotides. The fewer nucleotides that are used in a PCR primer the less specific the primer may be for its target site. Short primer molecules generally require lower temperatures to form sufficiently stable hybridization complexes with template to initiate primer extension.

The primers used herein may be selected to be substantially complementary to the different strands of each specific sequence to be synthesized or amplified. Accordingly, the primer may contain at its 3' terminus a nucleotide sequence sufficiently complementary to non-randomly hybridize with its respective template strand. Therefore, the primer sequence may not reflect the exact sequence of the template. For example, a non-complementary primer can be attached to the 5' end of the primer, with the remainder of the primer sequence being substantially complementary to the strand.

Such non-complementary primers might code for a site for protein binding or simply be used to adjust the reading frame of the codons. Alternatively, noncomplementary bases or longer sequences can be interspersed into the primer, provided the primer sequence has sufficient complementarity with the sequence of the template strand to allow hybridization to occur so that an extension product can be formed under nucleotide polymerizing conditions.

Sommer, et al., Nucleic Acid Res., 17:6749 (1989), which is incorporated in its entirety herein by reference, reports that primers having as little as a 3 nucleotide exact match at the 3' end are capable of specifically initiating primer extension products, although less nonspecific hybridization occurs when the primer contains more nucleotides at the 3' end having exact complementarity with the template sequence. Therefore, a substantially complementary primer as used herein may contain at its 3' end at least 3 nucleotides having exact complementarity to the template sequence.

The primer may be provided in single-stranded form for maximum efficiency, but may alternatively be double-stranded. If double-stranded, the primer may be first treated to separate its strands before being used to prepare extension products. The primer may be a deoxyribonucleic acid (oligodeoxyribonucleotide) or a ribonucleic acid (oligoribonucleotide). The primer may also be a combination of an oligoribonucleotide and an oligodeoxyribonucleotide.

Nucleic acid primers can be prepared by a variety of methods including de novo chemical synthesis. De novo chemical synthesis of a polynucleotide can be conducted using any suitable method, such as, for example, the phosphotriester or phosphodiester methods. See Narang et al, Meth. Enzymol., 68:90, (1979); U.S. Pat. No. 4,356,270; Itakura et al, Ann. Rev. Biochem., 53:323–56 (1989); and Brown et al, Meth. Enzymol., 68:109, (1979); Matteucci et al., J. Am. Chem. Soc., 103:3185 (1981) each patent and publication of which is incorporated in its entirety herein by reference. Primers may also be nucleic acid fragments derived from restriction endonuclease digest of larger double-stranded nucleic acids and strand separation or obtained by enzymatic synthesis using a nucleic acid template, though the method of preparation is not important.

Template nucleic acid sequences to be hybridized in the present methods can be present in any nucleic acid-containing sample so long as the sample is in a form, with respect to purity and concentration, compatible with a nucleic acid hybridization reaction. Isolation of nucleic acids to a degree suitable for hybridization is generally known and can be accomplished for nucleic acid from any nucleic acid containing source. For example, nucleic acids can be isolated from a variety of nucleic acid-containing samples including bacteria, plants, viruses, body tissue, such as skin, muscle, hair, and the like, and body fluids such as blood, plasma, urine, amniotic fluids, cerebral spinal fluids, and the like. See, for example, Sambrook et al, Molecular Cloning: A Laboratory Manual, Cold Spring Harbor Laboratory (1989); and Ausubel et al, Current Protocols in Molecules Biology, John Wiley and Sons (1987).

The hybridization reaction mixture may be maintained under hybridizing conditions for a time period sufficient for the primer to at least partially hybridize to complementary nucleic acid sequences present in the sample.

The phrase "hybridizing conditions" and its grammatical equivalents, when used with a maintenance time period, indicates subjecting the hybridization reaction admixture, in the context of the concentrations of reactants and accompanying reagents in the admixture, to time, temperature and pH conditions sufficient to allow the primer to anneal with the template sequence, typically to form a nucleic acid duplex. Such time, temperature and pH conditions required to accomplish hybridization depend, as is well known in the art, on the length of the primer to be hybridized, the degree of complementarity between the primer and the template, the percent GC content of the polynucleotide, the stringency of hybridization desired, and the presence of salts or additional reagents in the hybridization reaction admixture as may affect the kinetics of hybridization. Methods for optimizing hybridization conditions for a given hybridization reaction admixture are well known in the art. Typical hybridizing conditions include the use of solutions buffered to pH values between about 4 and about 9, and may be carried out at temperatures from about 18° C. to about 75° C. and for time periods from about 0.1 seconds to about 48 hours.

Hybridization can be carried out entirely in solution, in which both the primer and template sequences to be hybridized are present in soluble forms in solution or by use of a matrix that is insoluble in the reaction medium to which either the primer or template is bound.

Also contemplated are hybridization reactions such as those conducted for a reverse transcription of isolated mRNA or viral RNA to form cDNA, dideoxy sequencing and other procedures using primer extension reactions in which primer hybridization is a first step. For example, a hybridization reaction in which the template is amplified via a polymerase chain reaction (PCR) may be used.

Where the nucleic acid containing a template sequence is in a double-stranded (ds) form the dsDNA may first be denatured, as, for example, by heating or alkali treatment, prior to conducting the hybridization reaction. The denaturation of the dsDNA can be carried out prior to admixture formation with a primer to be hybridized, or it can be carried out after the admixture of the dsDNA with the primer is formed. Where the primer itself is provided as a double-stranded molecule, it too can be denatured prior to admixture, or it can be denatured concurrently with the template-containing dsDNA.

The nucleic acid is then subjected to a (first) primer extension reaction by treating (contacting) the nucleic acid with a DNA polymerase, for example, a heat stable DNA polymerase. The primer is capable of initiating a primer extension reaction by hybridizing to a specific nucleotide sequence. This is accomplished by mixing an effective amount of the primer with the template nucleic acid, and an effective amount of nucleotide reactants to form a primer extension reaction admixture. The admixture is maintained under polynucleotide synthesizing conditions for a time period, which may be predetermined, sufficient for the formation of a primer extension reaction product.

The primer extension reaction is performed using any suitable method. Generally polynucleotide synthesizing conditions are those wherein the reaction occurs in a buffered aqueous solution, at a pH of 4–9, for example, between about 7 and about 8. A molar excess of the primer may be admixed to the buffer containing the template strand. A molar excess may be used to improve the efficiency of the process. For example, a ratio may be in the range of about 5 to about 500 molar excess of primer to template DNA or about 5 to about 50 molar excess of primer to template DNA.

Deoxyribonucleotide triphosphates (dNTPs) dATP, dCTP, dGTP, and dTTP may also be admixed to the primer extension reaction admixture in amounts adequate to support the synthesis of primer extension products. The concentration of nucleotides used may depend on the size and number of products to be synthesized. The resulting solution is heated to about 96° C. to 100° C. for about 1 to about 10 minutes. After this heating period the solution may be allowed to cool to room temperature. To the mixture is added an enzyme for catalyzing the primer extension reaction, for example, a DNA polymerase, and the reaction is allowed to progress under conditions known in the art for the enzyme used. The polymerization reaction may occur at from room temperature up to a temperature above which the enzyme no longer functions efficiently. Thus, for example, if DNA polymerase is used as inducing agent, the temperature is generally no greater than about 40° C. unless the DNA polymerase used is heat-stable.

Suitable enzymes for this purpose include, for example, *E. coli* DNA polymerase I, Klenow fragment of *E. coli* DNA polymerase I, T4 DNA polymerase, T7 DNA polymerase, recombinant modified T7 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand.

Heat-stable (thermophilic) DNA polymerases are particularly useful for PCR as they are stable in an embodiment in which PCR is conducted in a single solution in which the temperature is cycled. Representative heat-stable polymerases are the DNA polymerases isolated from *Bacillus stearothermophilus* (Bio-Rad, Richmond, Calif.), *Thermus thermophilus* (FINZYME, ATCC #27634), Thermus species (ATCC #31674), *Thermus aquaticus* strain TV 1151B (ATCC #25105), *Sulfolobus acidocaldarius*, described by Bukhrashuili et al, Biochem. Biophys. Acta, 1008: 102–7 (1989) and by Elie et al, Biochem. Biophys. Actz, 951:261–7 (1988), *Thermus filiformis*. (ATCC #43280), the polymerase isolated from *Thermus flavus* (Molecular Biology Resources), and "Vent" polymerases (New England Biolabs). Many variants of heat stable DNA polymerases exist and many of these are available from a variety of sources including Applied Bibsystems Inc. (PE), Promega and Stratagene.

The enzyme selected may attach a single, overhanging nucleotide residue on the 3' end of a double-stranded nucleic acid. For example, the polymerase may attach a DAMP, dGMP, dCMP or dTMP to a 3' end of a DNA molecule.

This invention contemplates any double stranded nucleic acid segment produced by or exposed to an enzyme, for example, a polymerase, either in vitro or in vivo, in which a nucleotide is attached to the 3' end of the double stranded nucleic acid segment producing a 3' overhanging nucleotide on the otherwise double stranded molecule. For example, this invention contemplates any polymerase capable of producing a double-stranded nucleic acid having an overhanging 3' terminal nucleotide which may facilitate its insertion into a vector of the present invention. In one embodiment, DNA dependent DNA polymerases are used. In another embodiment, DNA dependent DNA polymerases and RNA dependent DNA polymerases are used. DNA dependent DNA polymerases include heat stable DNA polymerases.

Generally, the DNA synthesis will be initiated at the 3' end of each primer and proceed in the 5' direction along the template strand, until synthesis terminates, producing molecules that may be of different lengths.

The primer extension reaction product may then be subjected to a second primer extension reaction by treating it with a second polynucleotide synthesis primer having a preselected nucleotide sequence. The second primer is capable of initiating the second reaction by hybridizing to a nucleotide sequence found in the first primer extension product. This is accomplished by mixing the second primer with the first reaction admixture to form a PCR primer extension reaction admixture. A predetermined amount of each primer may be used to form the admixtures. The second admixture is maintained under polynucleotide synthesizing conditions for a time period, which may be predetermined, sufficient for the formation of a second primer extension reaction product.

In one embodiment, the first and second primer extension reactions are the first and second primer extension reactions in a polymerase chain reaction (PCR).

PCR may be carried out by cycling, i.e., sequentially performing in one admixture, the above described first and second primer extension reactions, each cycle comprising polynucleotide synthesis followed by denaturation of the double stranded polynucleotides formed. Methods and systems for amplifying a specific nucleic acid sequence are described in U.S. Pat. No. 4,683,195 and U.S. Pat. No. 4,683,202 and the teachings in PCR Technology, Erlich, ed., Stockton Press (1989); Falcona et al, Methods in Enzmol., 155:335–50 (1987); and Polymerase Chain Reaction, Erlich et al, eds., Cold Spring Harbor Laboratories Press (1989) each patent and publication of which is incorporated in its entirety herein by reference.

PCR may be carried out by cycling the following steps on one admixture: 1) denaturing step to form single-stranded templates, 2) hybridization step to hybridize a primer to DNA template, and 3) primer extension steps to form the extended product. PCR is performed in the above sequence (cycle) by changing the temperature of the PCR mixture to a temperature compatible with each step, in series.

The primer extension reaction conditions involve maintaining the reaction mixture for a time period and at a temperature sufficient for a DNA polymerase primer extension reaction to occur to produce primer extension products as is well known. Conditions for conducting a primer extension reaction are well known. In a PCR format, the extension time period may be carried out quickly to conveniently facilitate numerous cycles, for example, each cycle from about 0.1 second to 2 hours and at about 20° C. to 85° C. Conducting at least one cycle of PCR may result in the formation of amplified nucleic acid products. The PCR is typically conducted with about 20 to about 40 cycles, though more or fewer cycles may be employed.

Hybridizing conditions were described earlier and are suitable for use in the PCR format. However, hybridization may be conducted in short periods of time, for example from about 1 second to about 20 minutes. In certain instances, a hybridization time of about 2 minutes is used. Hybridization temperatures ranging from about 12° C. to 85° C. are common. The hybridization temperature selected may depend on, for example, length of the primer, % GC content of the primer, salt content of the reaction buffer and pH of the reaction buffer.

A PCR admixture may include one or more buffers and one or more metal ions such as magnesium, sodium, potassium or calcium. The admixture may also include a carrier such as bovine serum albumin.

Detection of amplified nucleic acid product can be accomplished by any of a variety of well-known techniques. In a one embodiment, the amplified product is separated on the basis of molecular weight by gel electrophoresis, and the separated products are then visualized by the use of nucleic acid specific stains which allow one to observe discrete species of resolved amplified product present in the gel. Numerous nucleic acid specific stains exist and would be suitable to visualize the electrophoretically separated nucleic acids. Examples of these stains include ethidium bromide and acridine orange.

Alternative methods suitable to detect an amplified nucleic acid product include hybridization-based detection means that use a labeled polynucleotide probe capable of hybridizing to an amplified product. Exemplary of such detection means include Southern blot analysis, ribonuclease protection analysis using in vitro labeled polyribonucleotide probes, and similar methods for detecting nucleic acids having specific nucleotide sequences. See, for example, Ausubel et al., Current Protocols in Molecular Biology, John Wiley & Sons, 1987.

In one approach for detecting the presence of a specific nucleic acid sequence, deoxyribonucleotide triphosphates (dNTPs) used in the primer extension reaction include a label or indicating group that will render a primer extension product detectable. Typically such labels include radioactive atoms such as $^{32}P$, $^{35}S$, $^{33}P$, $^{14}C$ and $^{3}H$ chemically modified nucleotide bases, and the like.

Alternatives to radioactively labeled dNTPs are dNTPs that are chemically modified to contain metal complexing agents, biotin-containing groups, fluorescent compounds, and the like.

One useful metal complexing agent is a lanthanide chelate compound formed by a lanthanide metal and beta-diketonate ligands, the lanthanide being bound to the nucleic acid or polynucleotide via a chelate forming compound such as an EDTA-analogue so that a fluorescent lanthanide complex is formed. See U.S. Pat. Nos. 4,374,120, and 4,569,790, each of which is incorporated in its entirety herein by reference.

Biotin or acridine ester-labeled oligonucleotides and their use in polynucleotides have been described. See U.S. Pat. No. 4,707,404 which is incorporated in its entirety herein by reference. Useful fluorescent marker compounds include fluorescein, rhodamine, Texas Red, NBD and the like.

Numerous applications of the PCR-based amplification method are contemplated that will be readily apparent to one skilled in the art. For example, cloning mRNA through reverse transcription to produce cDNA can be made more sensitive by the use of PCR-based amplification of the produced cDNA.

As is well known in the art, the choice of vector to which a targt DNA sequence of the present invention is linked depends upon the functional properties desired, for example, protein expression, restriction fragment mapping or DNA sequencing, and upon the host cell to be transformed. These limitations are inherent in the art of constructing recombinant DNA molecules.

A vector contemplated by the present invention may be capable of directing at least the replication, transcription and expression, of a target DNA sequence cloned in the vector. The present vectors may contain convenient restriction sites for easy removal of the cloned target DNA sequence.

In one embodiment, a vector contemplated by the present invention includes a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons, for example ColEI, are well known in the art. In addition, those embodiments that include a prokaryotic replicon may also include a gene whose expression confers drug resistance to a bacterial host transformed therewith. Typical bacterial drug resistance genes are those that confer resistance to ampicillin, tetracycline, or kanamycin.

Those vectors which include a prokaryotic replicon can also include a prokaryotic promoter capable of directing the expression (transcription and/or translation) of DNA sequence cloned therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a PCR product molecule of the present invention. Typical of such vector plasmids are pUC18, pUC19, pBR322 and pBR329 available from Bio-Rad Laboratories, pPL, pKK223, pTZ18U, pTZ19U, and pT7T319U, available from Pharmacia, and Bluescript® and Bluescribe® vectors available from Stratagene.

Expression vectors compatible with eukaryotic cells, for example, those compatible with vertebrate cells, can also be used to form the recombinant DNA molecules of the present invention. Eukaryotic cell expression vectors are well known in the art and are available from several commercial sources. Typical of such vectors are pSVL and pKSV-10 (Pharmacia), pBPV-1/pML2d (International Biotechnologies, Inc.), and pTDT1 (ATCC, #31255). In one embodiment, expression vectors used to construct the rDNAs of the present invention include a selectable marker that is effective in a eukaryotic cell, for example, a drug resistance selection marker. One drug resistance marker is the gene whose expression results in neomycin resistance, i.e., the neomycin phosphotransferase (neo) gene. Southern et al., J. Mol. Appl. Genet., 1:327–341 (1982).

The use of retroviral expression vectors to form the rDNAs of the present invention is also contemplated. As used herein, the term "retroviral expression vector" refers to a DNA molecule that includes a promoter sequence derived from the long terminal repeat (LTR) region of a retrovirus genome.

In certain embodiments, the expression vector is a retroviral expression vector that is may be replication-incompetent in eukaryotic cells. The construction and use of retroviral vectors has been described by Sorge et al., Mol. Cell. Biol., 4:1730–37 (1984).

In the present invention, the selected vector in its linearized form will have a single nucleotide cohesive termini-complementary to the termini generated by the polymerase, for example, heat stable DNA polymerase used in PCR amplification. The nucleotide that is attached to the 3' end of the dsDNA molecule by an enzyme, for example, a DNA polymerase may be dependent upon the sequence of the primer or primers used in the PCR, the sequence of the template DNA and/or the enzyme used.

The linearized vectors which form the compositions of the present invention may be dephosphorylated. For example, when complementary nucleotides are used at each end of the linear vector, for example, dGMP at one 3' end and dCMP at the other 3' end, the 5' termini of the vector are dephosphorylated to minimize circularization of the linear vector without an inserted Target DNA sequence. Dephosphorylation may also be useful when vectors comprising a composition of the present invention include 3' overhanging nucleotides that are complementary between vectors. However, dephosphorylation is not required for use of any of the herein described compositions.

A vector of the present invention may be an expression vector, a cloning vector, a shuttle vector, and the like.

The linearized vectors of the present invention may be derived from circular vectors which include a removable linking fragment that joins the two ends of the linearized vector. The linearized vector may be generated by restriction of the circular vector at desired sites using the restriction enzymes described herein according to procedures well known in the art and available from commercial enzyme suppliers.

In one embodiment, the present invention is useful to clone a PCR target DNA sequence. overhanging nucleotides at each end of the target may serve as complementary overhangs which anneal to a single base overhang of the vectors of the present invention.

In another embodiment, the present invention is used to clone a cDNA fragment into a vector of the present invention. For example, the cDNA may be inserted into the vector in a directional manner. This can be accomplished by employing a primer polynucleotide containing a cleavage site such as a restriction endonuclease site to allow the overhanging 3' nucleotide to be cleaved off of one end of the cDNA. This restriction endonuclease site is used to insert this restriction endonuclease-cleaved end of the cDNA into the vector. The other end of the cDNA is inserted into the vector using the overhanging 3' corresponding nucleotide present on that end of the cDNA to facilitate insertion into a vector of the present invention having a protruding 5' TMP. This procedure allows the cDNA to be inserted into a vector in a directional manner facilitating the expression of the DNA cloned.

Several methods may be used to produce a linear vector included in a composition of the present invention. For example, a linker DNA segment may be included in a circular vector of the present invention. The linker may be produced and incorporated into the vectors of the invention by techniques familiar to those skilled in the art. The linker may include certain endonuclease restriction sites that, when cleaved with the corresponding restriction enzyme, will generate specific, single 3'-nucleotide overhangs at one or more ends of the vectors. Restriction sites useful to create the single 3'-nucleotide overhangs include those cleaved by AhdI, AspEI, Eam1105I, EclHKI and XcmI. The identity of the single overhanging nucleotides (dAMP, dGMP, dCMP or dTMP) may be predetermined. The linker for vectors of the present invention may be designed to have one or more restriction sites. It may be desirable to screen the above enzymes for their activities and ligation efficiencies in particular applications. These methods are well known to those skilled in the art.

In one embodiment, two restriction sites are included in the internal region of a polylinker of a present vector. When these sites are digested with endonuclease enzymes corresponding to the restriction sites the circular vector will yield a linear vector of the present invention with two incompatible single 3'-nucleotide overhangs plus a small DNA fragment. The small DNA fragment can be removed by separation techniques well known to those skilled in the art, for example, gel filtration.

In another embodiment, a linker segment included in a circular vector of the present invention includes a restriction site that yields complementary single 3'-nucleotide overhangs at each end of a linear vector of the present invention when cleaved with the corresponding restriction endonuclease.

In still another embodiment, the linker segment includes restriction sites that yield a vector with a single nucleotide overhang plus a blunt end when each is cleaved with a corresponding restriction enzyme. A small DNA fragment is also produce which can be removed by separation techniques well known to those skilled in the art, for example, gel filtration chromatography.

The single nucleotide overhang on the linear vector may be predetermined. Also, in certain instances, the linear vector may be 5' dephosphorylated prior to use, for example, to prevent recircularization, dimerization or concatemerization of the vector(s) comprising a composition of the present invention.

In certain instances of these embodiments, restriction sites that correspond to those employed in the linker may be found elsewhere in the vector. In these cases these restriction sites may be destroyed by methods known to those skilled in the art before the vector is used to produce a vector comprising a composition of the present invention.

Linear vectors of the present invention may also be produced by enzymatically adding a single nucleotide to the 3' end of a blunt end linear vector of the present invention. In one embodiment a circular vector is cleaved with a restriction endonuclease, for example, EcoRV, to produce a blunt end linear vector. The linear vector is contacted with an enzyme, for example, a DNA polymerase, dNTPs, and appropriate buffer known to those skilled in the art. The reaction will be performed at a temperature of between about 18° C. and 80° C. and for a time period of, for example, 5 seconds to 48 hours as may be determined by those skilled in the art. Factors which affect the reaction time and temperature include the type and amount of enzyme used. The dNTP(s) used in the reaction will be added to the 3' end of the linear vector. So if, for example, the desired overhanging nucleotide for each 3' end of a vector is dCMP, dCTP will be included in the reaction. More than one nucleotide may be used in this type of reaction. For example, a mix of the nucleotides may be used. Any and all possible combinations of nucleotides are included within the scope of this invention. These combinations include, for example, dCTP, dGTP and dTTP; dCTP and dGTP, dATP and dTTP; dGTP and dTTP; and dGTP and dATP.

In another embodiment vectors of the present invention are produced by cleaving a vector with one or more restriction enzymes to produce a linear vector with cohesive ends. The cohesive ends are then partially filled in using an enzyme such as a DNA polymerase or Klenow fragment to produce a linear vector with single 3'-nucleotide overhangs. For example, a vector may be cleaved at a BglI restriction site and the site would be filled in except for the terminal position. If the BglI site is designed for example, to have the sequence, 5' GCCTTGAAGGC 3' sequence, addition of A, G and C to the fill in reaction will produce a linear vector of the present invention with two single 3'-dAMP overhangs. Numerous restriction endonucleases exist which produce cohesive ends. A person skilled in the art can readily design many variations of this example based on other restriction enzymes.

Also contemplated by the present invention are RNA equivalents of the above-described recombinant DNA molecules.

The target DNA sequences which may include one or more overhanging 3'-dNMP are combined with linear vectors which contain one or more overhanging 3'-dNTPs. Alternatively, the invention contemplates 3'-dNMP, 3'-dNDP and/or 3'-dNTP overhanging nucleotides on a target DNA sequence and/or a DNA vector. In an admixture thereof a ligase may be added to effect ligation of the components. Any ligase is contemplated to perform the ligation reaction effectively using methods and conditions well known to those skilled in the art. An example of a ligase is T4 DNA ligase.

Volume exclusion agents may also be used to accelerate the ligation reaction.

Notably, it is also contemplated that certain nucleic acids, which are desired to be cloned, will have only one terminal 3'-dNMP residue per duplex. This situation may arise from incomplete reaction of a PCR polymerase with amplified product. However, the present invention anticipates such eventuality, and will allow direct cloning of monoligated (linear) recombinants as long as the nucleic acid desired to be cloned binds to at least one terminal 3'-dNMP residue presented by the vector. Additionally, transformation of cells with monoligated recombinant DNA molecules will likely occur normally in these cases with ligation at the second 3'-dNMP terminus occurring intracellularly.

The present invention also relates to introducing the recombinant DNA molecules of the present invention into host cells, by, for example, transformation or transfection. The host cell can be either prokaryotic or eukaryotic. Prokaryotic host cells used may be a strain of $E.$ $coli.$ Eukaryotic host cells include yeast and mammalian cells, for example, vertebrate cells such as those from a mouse, rat, monkey or human fibroblastic cell line. Examples of eukaryotic host cells are Chinese hamster ovary (CHO) cells available from the ATCC as CCL61 and NIH Swiss mouse-embryo cells NIH/3T3 available from the ATCC as CRL 1658. One means of effecting transformation is electroporation.

Transformation of appropriate host cells with a recombinant DNA molecule of the present invention is accomplished by well known methods that typically depend on the type of vector used. With regard to transformation of prokaryotic host cells, see, for example, Cohen et al., Proc. Natl. Acad. Sci. USA, 69:2110 (1972); and Sambrook et al., Molecular Cloning, A Laboratory Mammal, Cold Spring Harbor Laboratory, Cold Spring Harbor, N.Y. (1989). With regard to transformation of vertebrate cells with retroviral vectors containing rDNAs, see, for example, Sorge et al., Mol. Cell. Biol., 4:1730–37 (1984); Graham et al., Virol., 52:456 (1973); and Wigler et al., Proc. Natl. Acad. Sci. USA, 76:1373–76 (1979).

Successfully transformed cells, i.e., cells that contain a recombinant DNA molecule of the present invention, can be identified by well known techniques. For example, cells resulting from the introduction of an rDNA of the present invention can be cloned to produce monoclonal colonies. Cells from those colonies can be harvested, lysed and their DNA content examined for the presence of the rDNA using a method such as that described by Southern, J. Mol. Biol., 98:503 (1975) or Berent et al., Biotech., 3:208 (1985).

In addition, to directly assay for the presence of rDNA, successful transformation can be confirmed by well known immunological methods when the rDNA is capable of directing the expression of a subject polypeptide. For example, cells successfully transformed with a subject rDNA containing an expression vector produce a polypeptide displaying a characteristic antigenicity. Samples of a culture containing cells suspected of being transformed are harvested and assayed for a subject polypeptide using antibodies specific for that polypeptide antigen, such as those produced by an appropriate hybridoma.

Thus, in addition to the transformed host cells themselves, the present invention also contemplates a culture of those cells, for example, a monoclonal (clonally homogeneous) culture, or a culture derived from a monoclonal culture, in a nutrient medium. Nutrient media useful for culturing transformed host cells are well known in the art and can be obtained from several commercial sources. In embodiments wherein the host cell is mammalian, a serum-free medium may be used.

The present method entails a culture comprising a nutrient medium containing host cells transformed with a recombinant DNA molecule of the present invention that is capable of expressing a gene encoding a subject polypeptide. The culture is maintained for a time period sufficient for the transformed cells to express the subject polypeptide. The expressed polypeptide is then recovered from the culture.

Methods for recovering an expressed polypeptide from a culture are well known in the art and include fractionation of the polypeptide-containing portion of the culture using well known biochemical techniques. For instance, the methods of gel filtration, gel chromatography, ultrafiltration, electrophoresis, ion exchange, affinity chromatography and the like, such as are known for protein fractionations, can be used to isolate the expressed proteins found in the culture. In addition, immunochemical methods, such as immunoaffinity, immunoabsorption and the like can be performed using well known methods.

One embodiment of the present invention will employ the Lac Z' blue/white phenotype of $E.$ $coli$ to allow a visual assay for effective cloning. To use this assay method restriction sites are engineered in-phase with the Lac Z' reading frame. Thus, a DNA fragment inserted into this indicator gene disrupts normal translation of the beta-galactosidase protein resulting in white colony phenotypes on growth media containing the chromogenic dye XGAL.

In one embodiment, a vector of the present invention contains antibiotic resistance genes such as an ampicillin resistance gene or a kanamycin resistance gene. Any gene which confers drug resistance on the host cell may be used in accordance with this invention.

Many of the compounds and groups involved in the instant specification (e.g., nucleic acids) have a number of forms, particularly variably protonated forms, in equilibrium with each other. As the skilled practitioner will understand, representation herein of one form of a compound or group is intended to include all forms thereof that are in equilibrium with each other.

The compositions serving as host vectors can be packaged in kit form. As used herein, the term "package" refers to a solid matrix or material customarily utilized in a system and capable of holding within fixed limits one or more of the reagent components for use in a method of the present invention. Such materials include glass and plastic (e.g., polyethylene, polypropylene and polycarbonate) bottles, vials, paper, plastic and plastic-foil laminated envelopes and the like. Thus, for example, a package can be a glass vial used to contain the appropriate quantities of compositions of the invention which comprise vectors, polynucleotide primer(s), buffer(s) and/or salt(s), restriction enzyme(s), DNA polymerase, DNA ligase, or a subset or a combination thereof. An aliquot of each component sufficient to perform at least one cloning procedure will be provided in each container.

In one embodiment, the vector is operatively linked to a label, e.g., indicator gene, thereby providing a means to detect a target DNA sequence incorporated into a vector of the invention. Labels well known to those skilled in the art and include those discussed hereinbefore, especially the Lac Z' visual marker. Other selectable markers may be used and are well known in the art.

The site in the vector where a target DNA sequence is to be cloned may be flanked by restriction endonuclease sites that are unique to the vector to facilitate removal of the cloned target DNA from the vector.

Kits useful for producing a template-complement or for amplification or detection of a specific nucleic acid sequence using a primer extension reaction methodology also typically include, in separate containers within the kit, dAMP, dTMP, dGMP and/or dCMP, and other like agents for performing primer extension reactions.

The reagent species, indicating means or primer extension reaction reagents of any system described herein can be provided in solution, as a liquid dispersion or as a substantially dry powder, e.g., the plasmids may be provided in lyophilized form. Where the reagent species or indicating means is an enzyme, the enzyme's substrate can also be provided in a separate package of a system. A solid support and one or more buffers as are known in the art may also be included as separately packaged elements in this system.

The invention having been described, examples illustrating its practice are set forth below. These examples should not, however, be considered to limit the scope of the invention.

EXAMPLES

Example 1

Preparation of Linear Cloning Vectors

A cloning vector of the present invention is produced by modification to pUC19, a pre-existing vector. 50 ng of pUC19 is digested to completion with EcoRI and HindIII. The digested DNA is run on a preparative, 4% low melting agarose gel to remove the polylinker region of the vector that is released during the double-digest. The linear vector is recovered from the gel, by methodology well known to those skilled in art, and precipitated using ethanol. A new polylinker is produced by annealing two synthetic DNA sequences to produce a double strand DNA sequence which includes two XcmI sites which are separated by a 12 nucleotide span. XcmI is a restriction site which includes a 5 nucleotide sequence that can consist of any of the 4 standard nucleotides at each position, flanked by specific 3 nucleotide recognition sequences. Upon digestion, XcmI leaves a single 3' nucleotide overhang which consists of the center nucleotide of the variable five nucleotide sequence. Therefore XcmI allows for specified single nucleotide overhangs to be created on the linearized vectors.

The two XcmI sites are near the center of the polylinker and the pair is flanked by several restriction sites including EcoRI, BamHI, BglI, AscI and NotI. These restriction sites are located on both sides of the new synthetic polylinker in order to allow for the release of the cloned PCR product by digestion of the recombinant vector with a single restriction enzyme.

Figure 1:
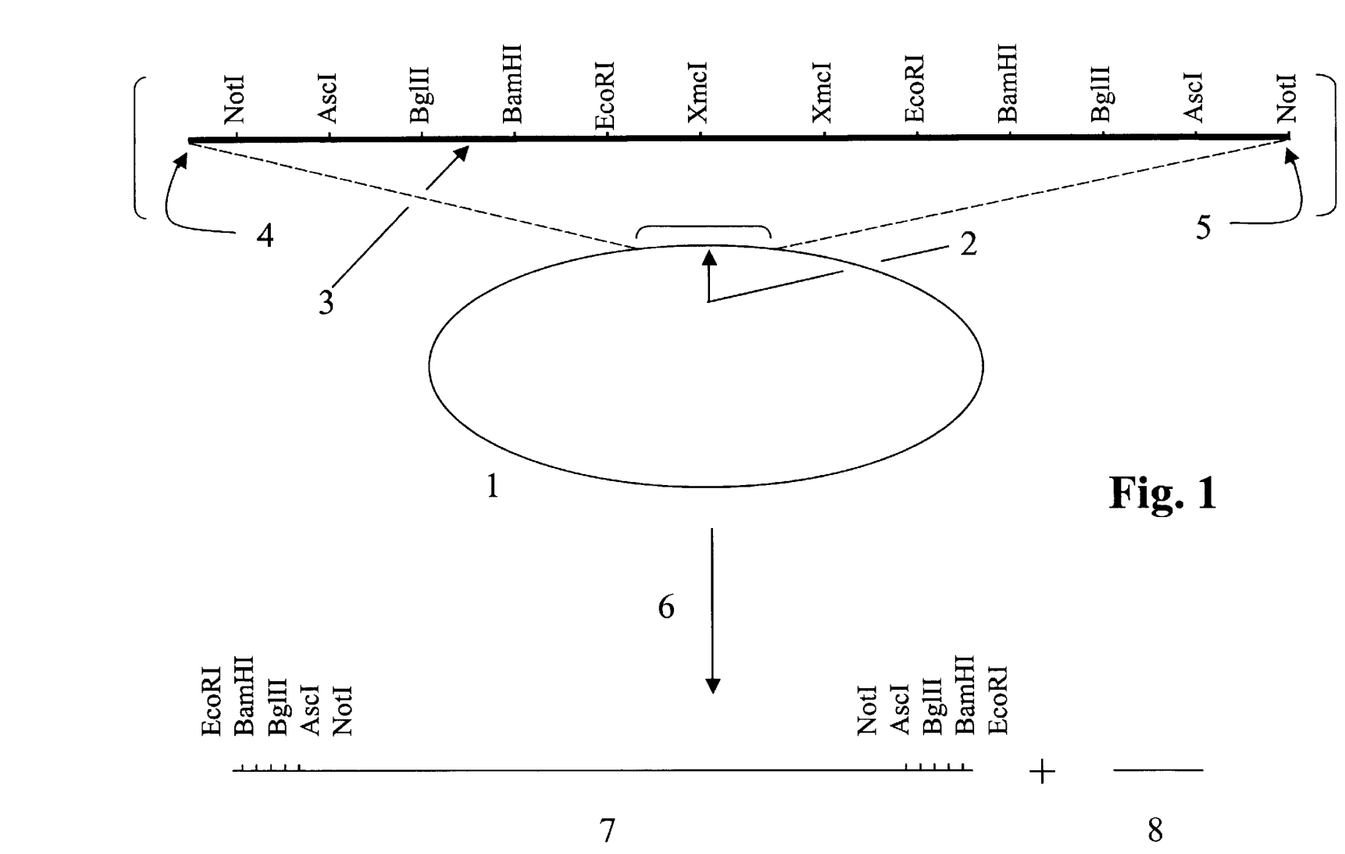
FIG. 1 is a diagrammatic representation of a vector of the present invention.

FIG. 1 shows a vector of the present invention. 1 is the vector in circular form. 2 and 3 are the polylinker in the vector. 2 points to the area under a bracket which spans the polylinker in the vector. 3 is an exploded view of the polylinker. 4 and 5 represent the regions of the new polylinker that are annealed and ligated to the EcoRI and BamHI sites (respectively) in the pUC19 vector after the native polylinker is removed from the pUC19. 6 represents a restriction digest of the vector with XcmI. 7 and 8 show the results of the restriction digest. 7 is a linear vector of the present invention. 8 is a small DNA fragment released from the vector which is between the two XcmI sites (see 3).

The new synthetic polylinker is produced such that the double stranded DNA polylinker sequence has ends that are able to anneal and subsequently ligate into the HindIII and EcoRI sites without regenerating these two restriction sites. In particular, nucleotides that are required to completely regenerate the two restriction sites are not present in the double stranded region at each end of the new polylinker. That is, a GC pair is substituted for the TA pair in the last nucleotide pair at the end of the linker that anneals to the pUC19 HindIII restriction site and a TA pair is likewise substituted for the GC pair in the last nucleotide pair at the end of the linker that anneals to the pUC19 EcoRI site.

Approximately 5 ng of recovered purified pUC19 (minus the native polylinker) is mixed with approximately 1 ng of new synthetic polylinker (non-phosphorylated). Ligation is conducted in a 10 ul reaction mix at 12° C. for 14 h utilizing 0.1 units (Weisse) of T4 DNA ligase in a standard buffer solution. 2 ul of ligation reaction mix is used in a standard transformation of competent C600 E. coli cells. For preparation of competent bacterial cells, a glycerol cell culture stock of the E. coli strain is thawed and added to 50 ml of liquid LB (Luria-Bertaini) media. The culture is preincubated at 37° C. for 1 hour, transferred to an incubator-shaker, and incubated for 3 hours further. The cells are pelleted by centrifugation, resuspended in a calcium chloride solution, and incubated in an ice-water bath. After another centrifugation step, the resulting cell pellet again is resuspended in a calcium chloride solution to yield the final competent cell suspension. Competent cells are stored at 4° C., for up to several days prior to use.

Transformation is performed using 2 ul of the ligation reaction mix. Heat shock transformation is used as is familiar to those skilled in the art.

After transformation, the cells are spread on plates of LB medium containing 2% agarose with 50 ug per ml ampicillin and are incubated overnight at 37° C. Approximately 120 colonies are present after an 18 hr incubation period, 6 of which are inoculated each into 6 ml of liquid LB medium containing 0.1 mg per ml ampicillin. These tubes are incubated overnight with shaking at 37° C. Vector minipreps are prepared by a modified alkaline lysis procedure. 1.0 ug of each vector is denature by alkaline denatuation and then precipitated using ethanol and sodium acetate. 50 ng of a 17 nucleotide primer, labeled for automated sequence analysis, designed to be complementary to the vector 84 base pairs upstream of the new polylinker, is added to each precipitated vector in a 20 ul quantity of TE buffer. After incubating at 37° C. for 2 hr, the vectors are sequenced using an automated DNA sequence analyzer. 6 of the 6 vectors are confirmed to have the correct polylinker sequence.

Preparations are also done as described above, but with only one XcmI site to produce linear vectors with a nucleotide overhanging each 3' end of the linearized vector.

The above procedure is performed 10 times with 10 different polylinkers designed to produce vectors with:

1) one 3' T overhang and one 3' G overhang;
2) one 3' T overhang and one 3' C overhang;
3) one 3' T overhang and one 3' A overhang;
4) one 3' G overhang and one 3' C overhang;
5) one 3' G overhang and one 3' A overhang;
6) one 3' C overhang and one 3' A overhang;
7) one 3' T overhang at each 3' end;
8) one 3' G overhang at each 3' end;
9) one 3' C overhang at each 3' end; and
10) one 3' A overhang at each 3' end.

For each of these constructs a large scale preparation is done which utilizes 2 liters of LB medium containing 0.1 mg per ml of ampicillin. The medium is inoculated with 5 ml of an actively growing culture of a transformant carrying a recombinant vector with a new polylinker region. Each two liter preparation is incubated at 37° C. with shaking for approximately 18 hr. The cells are collected by centrifugation and the vectors are prepared by alkaline lysis and CsCl gradient purification (Sambrook et al). Approximately 0.5 mg of each vector is recovered for each clone.

0.1 mg of each clone is digested to completion utilizing approximately 100 units of XcmI under standard conditions.

Each digested clone is examined for completion of digest on a 1% analytical agarose gel. Each linearized vector is purified on a CsCl gradient. The linear vector is recovered, precipitated with ethanol and resuspended in nuclease free TE buffer at approximately 1.0 ug per ul.

The examples below include certain combinations of the above described cloning vectors. These are only examples and any and all of the 1000 combinations of these vectors are included within the scope of the invention.

Example 2

Comparative Cloning Efficiencies

Cloning Experiment 1

PCR primers are designed to amplify a nucleotide sequence of approximately 400 nucleotides in the tryptophanyl synthetase gene of *Saccharomyces cerevisiae*. The nucleotide sequence of the primers is selected based on the previously reported sequence of the *S. cerevisiae* tryptophanyl synthetase gene.

A standard PCR protocol is used with reaction conditions of: 50 mM KCl, 10 mM Tris-Cl (pH 8.3), 1.5 mM $MgCl_2$, 10 ng of genomic yeast DNA, 100 ng of each primer, 2 units of Taq DNA polymerase in a 20 ul reaction mix. 35 cycles are performed with cycle times of:

| | |
|---|---|
| Denaturation | 96° C., 15 seconds |
| Primer Annealing | 55° C., 30 seconds |
| Primer Extension | 72° C., 1.5 minutes |

After completion of, the PCR reaction, a 2 ul aliquot of PCR reaction mix is used for ligation with each cloning vector, or cloning vector composition, listed.

The following components are combined and incubated overnight at 4° C.:

| | | |
|---|---|---|
| PCR Product | 2 ul | |
| linearized cloning vector DNA | 2 ul | (10 ng/ul) |
| 10X ligation buffer (NEB) | 1 ul | |
| T4 DNA ligase (NEB 202L) | 1 ul | (400 U/ul) |
| sterile ddH20 | q.s. | |
| | 10 ul | |

For preparation of competent bacterial cells, a glycerol cell culture stock of the C600 *E. coli* cells is thawed and added to 50 ml of liquid media. The culture is preincubated at 37° C. for 1 hour, transferred to an incubator-shaker, and is incubated for 3 hours further. The cells are pelleted by centrifugation, resuspended in a calcium chloride solution, and incubated in an ice-water bath. After another centrifugation step, the resulting cell pellet again is resuspended in calcium chloride to yield the final competent cell suspension. Competent cells are stored at 4° C., for up to several days prior to use.

Transformation is performed using 2 ul of the ligation reaction mix. Heat shock transformation is used as is familiar to those skilled in the art. The cells are spread on plates of LB medium containing 2% agarose with 50 ug per ml ampicillin, 50 ug/ml 0.5 mM IPTG and 40 ug/ml X-Gal and are incubated overnight at 37° C. Potential positive transformants are identified using blue white screening. Vectors isolated from white colonies are screened for inserts of the appropriate size by restriction digest analysis.

The cloning experiment is done in triplicate using: 1) a T-T vector; 2) a dephosporylated, blunt end cloning vector; and 3) a composition of a T-T vector and a T-C vector. The results are as follows:

T-T 6 colonies—5 blue, 1 white

Vector DNA is prepared from the white colony by a standard mini-prep technique. Insert of a cloned DNA fragment is screened for by digestion with NotI and electrophoresis on a minigel. No insert is present.

Blunt End 16 colonies—16 blue

T-T, T-C 42 colonies—6 blue, 36 white

Vector DNA is prepared from 8 of the white colonies by a standard mini-prep technique. Insert of a cloned DNA fragment is screened for by digestion with NotI and electrophoresis on a minigel. Taking into account the nucleotides added to the insert from the polylinker region of the vector, a DNA insert of approximately 400 nucleotides in length is present in 7 of the 8 clones.

Cloning Experiment 2

PCR primers are designed to amplify a nucleotide sequence of approximately 220 nucleotides in the ampicillin resistance gene of pBR322. The nucleotide sequence of the primers is selected based on the previously reported sequence of the gene.

Cloning, transformation and analysis of the cloned PCR product is done essentially as described in cloning experiment 1.

The cloning is done in triplicate using: 1) a T-T vector; 2) a dephosporylated, blunt end cloning vector; and 3) a composition of a T-T vector and a T-G vector. The results are as follows:

T-T 12 colonies—8 blue, 4 white

Vector DNA is prepared from the white colonies by a standard mini-prep technique. Insert of a cloned DNA fragment is screened for by digestion with NotI and electrophoresis on a minigel. A DNA insert of approximately 220 base pairs is present in one of the clones.

Blunt End Vector 14 colonies—12 blue, 2 white

Vector DNA is prepared from the white colonies by a standard mini-prep technique. Insert of a cloned DNA fragment is screened for by digestion with NotI and electrophoresis on a minigel. No insert is present in either clone.

T-T, T-G 39 colonies—8 blue, 31 white

Vector DNA is prepared from 8 of the white colonies by a standard mini-prep technique. Insert of a cloned DNA fragment is screened for by digestion with NotI and electrophoresis on a minigel. A DNA insert of approximately 220 nucleotides in length is present in 8 of the 8 clones.

Cloning Experiment 3

PCR primers are designed to amplify a nucleotide sequence of approximately 360 nucleotides in a human globin gene. The nucleotide sequence of the primers is selected based on the previously reported sequence of the gene.

Cloning, transformation and analysis of the cloned PCR product is done essentially as described in cloning experiment 1.

The cloning is done in duplicate using: 1) a T-T vector; 2) a composition mixture of A-A vector, C-C vector, T-C vector and T-G vector. The results are as follows:

T-T 2 colonies—2 blue, 0 white

A-A, C-C, T-C, T-G 31 colonies—5 blue, 26 white

Vector DNA is prepared from 8 of the white colonies by a standard mini-prep technique. Insert of a cloned DNA fragment is screened for by digestion with NotI and electrophoresis on a minigel. A DNA insert of approximately 360 nucleotides in length is present in 7 of the 8 clones.

Cloning Experiment 4

PCR primers are designed to amplify a nucleotide sequence of approximately 680 nucleotides in the human c-myc locus. The nucleotide sequence of the primers is selected based on the previously reported sequence of the gene.

Cloning, transformation and analysis of the cloned PCR product is done essentially as described in cloning experiment 1.

The cloning is done in duplicate using: 1) a T-T vector; 2) a composition mixture of T-G vector, T-T vector, T-A vector and T-C vector. The results are as follows:

T-T 22 colonies—18 blue, 4 white

Vector DNA is prepared from the white colonies by a standard mini-prep technique. Insert of a cloned DNA fragment is screened for by digestion with NotI and electrophoresis on a minigel. No insert is present in any of the 4 clones.

T-G, T-T, T-A, T-C 23 colonies—6 blue, 17 white

Vector DNA is prepared from 8 of the white colonies by a standard mini-prep technique. Insert of a cloned DNA fragment is screened for by digestion with NotI and electrophoresis on a minigel. A DNA insert of approximately 680 nucleotides in length is present in eight of the eight clones.

Cloning Experiment 5

PCR primers are designed to amplify a nucleotide sequence of approximately 180 nucleotides in a Tetrahymena ribosomal RNA gene. The nucleotide sequence of the primers is selected based on the previously reported sequence of the gene.

Cloning, transformation and analysis of the cloned PCR product is done essentially as described in cloning experiment 1.

The cloning is done in duplicate using: 1) a T-T vector; 2) a composition mixture of T-T vector, T-A vector and T-C vector. The results are as follows:

T-T 62 colonies—5 blue, 57 white

Vector DNA is prepared from 8 of the white colonies by a standard mini-prep technique. Insert of a cloned DNA fragment is screened for by digestion with NotI and electrophoresis on a minigel. A DNA insert of approximately 180 nucleotides in length is present in six of the eight clones.

T-T, T-C, T-A 58 colonies—4 blue, 54 white

Vector DNA is prepared from 8 of the white colonies by a standard mini-prep technique. Insert of a cloned DNA fragment is screened for by digestion with NotI and electrophoresis on a minigel. A DNA insert of approximately 180 nucleotides in length is present in six of the eight clones.

Cloning Experiment 6

PCR primers are designed to amplify a nucleotide sequence of approximately 160 nucleotides in a histone gene in Xenopus borealis. The nucleotide sequence of the primers is selected based on the previously reported sequence of the gene.

Cloning, transformation and analysis of the cloned PCR product is done essentially as described in cloning experiment 1.

The cloning is done in triplicate using: 1) a T-T vector; 2) a composition mixture of T-T vector, C-C vector and T-C vector. The results are as follows:

T-T 2 colonies—2 blue, 0 white

T-T, C-C, T-C 31 colonies—5 blue, 26 white

Vector DNA is prepared from 8 of the white colonies by a standard mini-prep technique. Insert of a cloned DNA fragment is screened for by digestion with NotI and electrophoresis on a minigel. A DNA insert of approximately 160 nucleotides in length is present in 7 of the eight clones.

Cloning Experiment 7

PCR primers are designed to amplify a nucleotide sequence of approximately 80 nucleotides in the Toll gene of a recombinant strain of *Pseudomonas aeruginosa*. The nucleotide sequence of the-primers is selected based on the previously reported.sequence of the gene.

Cloning, transformation and analysis of the cloned PCR product is done essentially as described in cloning experiment 1.

The cloning is done in duplicate using: 1) a T-T vector; 2) a composition mixture of T-T vector, C-C vector and T-C vector. The results are as follows:

T-T 97 colonies—22 blue, 75 white

Vector DNA is prepared from 8 of the white colonies by a standard mini-prep technique. Insert of a cloned DNA fragment is screened for by digestion with NotI and electrophoresis on a minigel. A DNA insert of approximately 80 nucleotides in length is present in 7 of the eight clones.

T-T, C-C, T-C 112 colonies—18 blue, 94 white

Vector DNA is prepared from 8 of the white colonies by a standard mini-prep technique. Insert of a cloned DNA fragment is screened for by digestion with NotI and electrophoresis on a minigel. A DNA insert of approximately 80 nucleotides in length is present in 7 of the eight clones.

Cloning Experiment 8

PCR primers are designed to amplify a nucleotide sequence of approximately 350 nucleotides in the S1 nuclease locus of an Aspergillus species. The nucleotide sequence of the primers is selected based on the previously reported sequence of the gene.

Cloning, transformation and analysis of the cloned PCR product is done essentially as described in cloning experiment 1.

The cloning is done in triplicate using: 1) a T-T vector; 2) a composition mixture of T-G vector, T-T vector, T-A vector and T-C vector. The results are as follows:

T-T.

12 colonies—11 blue, 1 white

Vector DNA is prepared from the white colony by a standard mini-prep technique. Insert of a cloned DNA fragment is screened for by digestion with NotI and electrophoresis on a minigel. No insert is present in the clones.

T-G, T-T, T-A, T-C, C-C 128 colonies—16 blue, 112 white

Vector DNA is prepared from 8 of the white colonies by a standard mini-prep technique. Insert of a cloned DNA fragment is screened for by digestion with NotI and electrophoresis on a minigel. A DNA insert of approximately 350 nucleotides in length is present in eight of the eight clones.

While this invention has been described with respect to various specific examples and embodiments, it is to be understood that the invention is not limited thereto and that it can be variously practiced with the scope of the following claims.

What is claimed is:

1. A composition comprising two or more linear DNA molecules capable of self-replicating when circularized, the linear DNA molecules comprising a single overhanging nucleotide at each 3' end, wherein a pair of overhanging nucleotides of a linear DNA molecule of the composition are different than a pair of overhanging nucleotides of another linear DNA molecule of the composition.

2. The composition of claim 1 wherein the two or more linear DNA molecules are selected from the group consisting of a linear DNA molecule comprising an overhanging dTMP at each 3' end, a linear DNA molecule comprising an overhanging dGMP at each 3' end, a linear DNA molecule comprising an overhanging dCMP at each 3' end, a linear DNA molecule comprising an overhanging dAMP at each 3' end, a linear DNA molecule comprising an overhanging dTMP at a 3' end and an overhanging dAMP at another 3' end, a linear DNA molecule comprising an overhanging dTMP at a 3' end and an overhanging dGMP at another 3' end, a linear DNA molecule comprising an overhanging dTMP at a 3' end and an overhanging dCMP at another 3' end, a linear DNA molecule comprising an overhanging dAMP at a 3' end and an overhanging dGMP at another 3' end, a linear DNA molecule comprising an overhanging dAMP at a 3' end and an overhanging dCMP at another 3' end and a linear DNA molecule comprising an overhanging dGMP at a 3' end and an overhanging dCMP at another 3' end.

3. The composition of claim 1 wherein the two or more linear DNA molecules are a linear DNA molecule comprising an overhanging dTMP at a 3' end and an overhanging dCMP at another 3' end and a linear DNA molecule comprising an overhanging dTMP at each 3' end.

4. The composition of claim 1 wherein the two or more linear DNA molecules are a linear DNA molecule comprising an overhanging dCMP at each 3' end and a linear DNA molecule comprising an overhanging dTMP at a 3' end and an overhanging dCMP at another 3' end.

5. The composition of claim 1 wherein the two or more linear DNA molecules are a linear DNA molecule comprising an overhanging dTMP at a 3' end and an overhanging dCMP at another 3' end, a linear DNA molecule comprising an overhanging dCMP at each 3' end and a linear DNA molecule comprising an overhanging dTMP at each 3' end.

6. The composition of claim 1 wherein the linear DNA molecules comprise a linearized vector.

7. The composition of claim 6 wherein the vector is selected from the group consisting of a plasmid, a phagemid, a bacteriophage, a prokaryotic expression vector, a eukaryotic vector, a eukaryotic expression vector and a virus.

8. The composition of claim 6 wherein the vector is a phagemid.

9. The composition of claim 1 further comprising a polymerase chain reaction nucleic acid product.

10. The composition of claim 1 further comprising a competent cell.

11. The composition of claim 1 wherein the two or more linear DNA molecules are present in a ratio which maximizes a percentage of positive clones in a ligation reaction comprising the two or more linear DNA molecules and a polymerase chain reaction nucleic acid product.

12. A composition comprising a linearized vector comprising a single overhanging dTMP at a 3' end and a single overhanging dCMP at another 3' end and a linearized vector comprising a single overhanging dTMP at each 3' end.

13. The composition of claim 12 further comprising a linearized vector comprising a single overhanging dCMP at each 3' end.

14. The composition of claim 12 wherein the vector is selected from the group consisting of a plasmid, a phagemid, a bacteriophage, a prokaryotic expression vector, a eukaryotic vector, a eukaryotic expression vector and a virus.

15. The composition of claim 12 further comprising a competent cell.

16. The composition of claim 12 further comprising a polymerase chain reaction nucleic acid product.

17. A method of cloning a DNA molecule which is produced by a polymerase chain reaction comprising:

subjecting a DNA molecule to a polymerase chain reaction producing a nucleic acid product, ligating the nucleic acid product in a mixture comprising the nucleic acid product and two or more linear DNA molecules capable of self-replicating when circularized, the linear DNA molecules comprising a single overhanging nucleotide at each 3' end, wherein a pair of overhanging nucleotides of a linear DNA molecule of the composition are different than a pair of overhanging nucleotides of another linear DNA molecule of the composition.

18. The method of claim 17 wherein the two or more linear DNA molecules are selected from the group consisting of a linear DNA molecule comprising an overhanging dTMP at each 3' end, a linear DNA molecule comprising an overhanging dGMP at each 3' end, a linear DNA molecule comprising an overhanging dCMP at each 3' end, a linear DNA molecule comprising an overhanging dAMP at each 3' end, a linear DNA molecule comprising an overhanging dTMP at a 3' end and an overhanging dAMP at another 3' end, a linear DNA molecule comprising an overhanging dTMP at a 3' end and an overhanging dGMP at another 3' end, a linear DNA molecule comprising an overhanging dTMP at a 3' end and an overhanging dCMP at another 3' end, a linear DNA molecule comprising an overhanging dAMP at a 3' end and an overhanging dGMP at another 3' end, a linear DNA molecule comprising an overhanging dAMP at a 3' end and an overhanging dCMP at another 3' end and a linear DNA molecule comprising an overhanging dGMP at a 3' end and an overhanging dCMP at another 3' end.

19. The method of claim 17 wherein the two or more linear DNA molecules are a linear DNA molecule comprising an overhanging dTMP at a 3' end and an overhanging dCMP at another 3' end and a linear DNA molecule comprising an overhanging dTMP at each 3' end.

20. The method of claim 17 wherein the two or more linear DNA molecules are a linear DNA molecule comprising an overhanging dTMP at a 3' end and an overhanging dCMP at another 3' end, a linear DNA molecule comprising an overhanging dCMP at each 3' end and a linear DNA molecule comprising an overhanging dTMP at each 3' end.

21. The method of claim 17 wherein the linear DNA molecule comprises a linearized vector.

22. The method of claim 17 further comprising transforming the mixture into host cells.

23. The method of claim 17 wherein the two or more linear DNA molecules are present in a ratio which maximizes a percentage of positive clones.

24. A kit for cloning of nucleic acids wherein the kit comprises:

a container which includes a composition comprising two or more linear DNA molecules capable of self-replicating when circularized, the linear DNA molecules comprising a single overhanging nucleotide at each 3' end, wherein a pair of overhanging nucleotides of a linear DNA molecule of the composition are different than a pair of overhanging nucleotides of another linear DNA molecule of the composition.

25. The kit of claim 24 wherein the two or more linear DNA molecules are selected from the group consisting of a linear DNA molecule comprising an overhanging dTMP at each 3' end, a linear DNA molecule comprising an overhanging dGMP at each 3' end, a linear DNA molecule comprising an overhanging dCMP at each 3' end, a linear DNA molecule comprising an overhanging dAMP at each 3' end, a linear DNA molecule comprising an overhanging dTMP at a 3' end and an overhanging dAMP at another 3' end, a linear DNA molecule comprising an overhanging dTMP at a 3' end and an overhanging dGMP at another 3' end, a linear DNA molecule comprising an overhanging dTMP at a 3' end and an overhanging dCMP at another 3' end, a linear DNA molecule comprising an overhanging dAMP at a 3' end and an overhanging dGMP at another 3' end, a linear DNA molecule comprising an overhanging dAMP at a 3' end and an overhanging dCMP at another 3' end and a linear DNA molecule comprising an overhanging dGMP at a 3' end and an overhanging dCMP at another 3' end.

26. The kit of claim 24 wherein the two or more linear DNA molecules are a linear DNA molecule comprising an overhanging dTMP at a 3' end and an overhanging dCMP at another 3' end and linear DNA molecule comprising an overhanging dTMP at each 3' end.

27. The kit of claim 24 wherein the two or more linear DNA molecules are a linear DNA molecule comprising an overhanging dTMP at a 3' end and an overhanging dCMP at another 3' end, a linear DNA molecule comprising an overhanging dCMP at each 3' end and a linear DNA molecule comprising an overhanging dTMP at each 3' end.

28. The kit of claim 24 wherein the linear DNA molecules comprise a linearized vector.

29. The kit of claim 24 further comprising a container which includes a competent cell.

30. The kit of claim 29 wherein the competent cell is a prokaryote.

31. The kit of claim 29 wherein the competent cell is an *E. coli*.

32. The kit of claim 24 wherein the two or more linear DNA molecules are present in a ratio which maximizes a percentage of positive clones in a ligation reaction comprising the two or more linear DNA molecules and a polymerase chain reaction nucleic acid product.

* * * * *